US012780761B2

(12) United States Patent
Cotte et al.

(10) Patent No.: US 12,780,761 B2
(45) Date of Patent: Nov. 3, 2026

(54) METHOD FOR OLIGOMERISATION IN A REACTOR COMPRISING VARIABLE-DIAMETER ZONES, INCLUDING A STEP OF RECYCLING A PRE-COOLED SOLVENT

(71) Applicant: IFP Energies nouvelles, Rueil-Malmaison (FR)

(72) Inventors: Olivier Cotte, Rueil-Malmaison Cedex (FR); Pierre-Alain Breuil, Rueil-Malmaison Cedex (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 204 days.

(21) Appl. No.: 18/564,264

(22) PCT Filed: May 24, 2022

(86) PCT No.: PCT/EP2022/064008
§ 371 (c)(1),
(2) Date: Nov. 27, 2023

(87) PCT Pub. No.: WO2022/248449
PCT Pub. Date: Dec. 1, 2022

(65) Prior Publication Data

US 2024/0239725 A1 Jul. 18, 2024

(30) Foreign Application Priority Data

May 28, 2021 (FR) ....................................... 2105617

(51) Int. Cl.
*C07C 2/30* (2006.01)
*B01J 8/18* (2006.01)
(Continued)

(52) U.S. Cl.
CPC ............... *C07C 2/30* (2013.01); *B01J 8/1836* (2013.01); *B01J 8/22* (2013.01); *C07C 2/24* (2013.01);
(Continued)

(58) Field of Classification Search
CPC ...................... B01J 8/1836; B01J 2208/00256
See application file for complete search history.

(56) References Cited

U.S. PATENT DOCUMENTS 4,615,998 A 10/1986 Le Quan et al.
5,962,761 A * 10/1999 Sechrist ................ B01D 3/009 585/524

(Continued)

FOREIGN PATENT DOCUMENTS

CN 1048976 C * 2/2000 ................ B01J 3/04
CN 210855896 U 6/2020

(Continued)

OTHER PUBLICATIONS

Machine Translation of CN1048976C (Year: 2000).*
International Search report PCT/EP2022/064008 dated Sep. 29, 2022 (pp. 1-2).

*Primary Examiner* — Ellen M Mcavoy
*Assistant Examiner* — Ming Cheung Po
(74) *Attorney, Agent, or Firm* — Csaba Henter; MILLEN, WHITE, ZELANO & BRANIGAN, P.C.

(57) ABSTRACT

The present invention relates to a process for oligomerization in a reactor with zones of variable diameters comprising a step of recycling a precooled solvent.

17 Claims, 4 Drawing Sheets

(51) Int. Cl.

| | |
|---|---|
| ***B01J 8/22*** | (2006.01) |
| ***B01J 31/02*** | (2006.01) |
| ***B01J 31/22*** | (2006.01) |
| ***C07C 2/24*** | (2006.01) |

(52) U.S. Cl.

CPC . *B01J 2208/00256* (2013.01); *C07C 2523/26* (2013.01); *C07C 2531/14* (2013.01)

(56) References Cited

U.S. PATENT DOCUMENTS

| | | | |
|---|---|---|---|
| 8,816,147 | B2 | 8/2014 | Vinel et al. |
| 9,931,622 | B2 | 4/2018 | Magna et al. |
| 10,150,108 | B2 | 12/2018 | Magna et al. |
| 10,646,860 | B2 | 5/2020 | Breuil et al. |
| 11,207,657 | B2 | 12/2021 | Augier et al. |
| 2007/0185362 | A1* | 8/2007 | Lattner ..................... C07C 2/36 585/521 |
| 2007/0213573 | A1* | 9/2007 | Ross ...................... B01J 8/0065 585/242 |
| 2013/0158321 | A1 | 6/2013 | Olivier-Bourbigou et al. |
| 2018/0318819 | A1 | 11/2018 | Breuil et al. |

FOREIGN PATENT DOCUMENTS

| | | | | |
|---|---|---|---|---|
| DE | 4338414 | C1 | 3/1995 | |
| EP | 2703373 | A1 | 3/2014 | |
| FR | 3068620 | A1 | 1/2019 | |
| WO | WO-2013116922 | A1 * | 8/2013 | ............... C07C 2/32 |

* cited by examiner

METHOD FOR OLIGOMERISATION IN A REACTOR COMPRISING VARIABLE-DIAMETER ZONES, INCLUDING A STEP OF RECYCLING A PRE-COOLED SOLVENT

TECHNICAL FIELD

The present invention relates to a process for the oligomerization of an olefinic feedstock carried out in a reactor with zones of variable diameters, in which a solvent fraction resulting from a downstream separation step is cooled and recycled. In particular, the present invention relates to a process for the oligomerization of a gaseous olefinic feedstock, preferably of gaseous ethylene, to give linear α-olefins such as but-1-ene, hex-1-ene or oct-1-ene, or a mixture of linear α-olefins.

PRIOR ART

The invention relates to the field of oligomerization directed towards producing α-olefins which are used as comonomers in processes for producing polyethylene. The oligomerization reaction is commonly performed in a homogeneous catalysis process in the liquid phase in a two-phase gas/liquid reactor, in general with implementation in a bubble column.

The oligomerization reaction is highly exothermic; it is common to regulate the reaction temperature by use of external cooling. A reactor can be coupled to one or more recirculation loops in order to withdraw a liquid fraction, cool it via an exchanger or exchangers, and reintroduce it into the reactor. Said recirculation loop makes it possible to obtain a good homogeneity of the concentrations and to control the temperature throughout the reaction volume. Patent EP 2 703 373 proposes a process for the trimerization of ethylene to give hex-1-ene that makes it possible to reduce the cost of the plants by limiting the energy consumption linked to the recirculation loop. For this, a bottom fraction composed mainly of solvent resulting from the separation section is used in the thermal exchanger of the recirculation loop and also for the reboiling of the bottom of a column of the separation section.

One drawback encountered during the use of a gas/liquid two-phase reactor in processes for the oligomerization for example of ethylene is the management of the gas headspace, corresponding to the upper part of the reactor in the gaseous state. Said gas headspace comprises gaseous compounds of low solubility in the liquid phase, compounds which are partially soluble in the liquid but which are inert, and also gaseous ethylene not dissolved in said liquid. The passage of gaseous ethylene from the liquid lower part of the reaction chamber to the gas headspace is a phenomenon referred to as breakthrough. In point of fact, the gas headspace is bled in order to remove said gaseous compounds. When the amount of gaseous ethylene present in the gas headspace is high, the bleeding of the gas headspace leads to a not insignificant loss of ethylene, which is detrimental to the productivity and to the cost of the oligomerization process. Furthermore, a significant breakthrough phenomenon means that a great deal of gaseous ethylene was not dissolved in the liquid phase and thus was not able to react, which is detrimental to the productivity and to the selectivity of the oligomerization process.

In order to improve the efficiency of the oligomerization process in terms of productivity and of cost, it is thus essential to limit the phenomenon of breakthrough of the ethylene in order to improve its conversion in said process, while at the same time maintaining good selectivity for the desired linear α-olefins.

In the field of the invention, those skilled in the art constantly seek to improve the oligomerization processes, notably by controlling the proportioning of the equipment having an impact on the performance and the cost of the process. They also seek to reduce the cost of the plants used to carry out the oligomerization.

The applicant has discovered a process for the oligomerization of an olefinic feedstock carried out in a reactor with zones of variable diameter and in which a solvent fraction resulting from a downstream separation step is cooled and recycled so as to partly control the exothermicity generated by the oligomerization reaction in the reactor. The aim of the present invention is to improve the process for the oligomerization of an olefinic feedstock, in particular ethylene, in a gas/liquid reactor. The invention seeks notably to improve the productivity/viability of the process, notably so as to avoid the phenomenon of breakthrough and/or to limit the investment and/or running costs of the process. The implementation of the recycling of a cooled solvent fraction from a separation section in the process according to the invention makes it possible to limit the size of the heat exchanger(s) used in at least one recirculation loop. The implementation of a reactor with zones of variable diameter according to the invention makes it possible to improve the dissolution of the gaseous olefinic feedstock and therefore to limit the breakthrough phenomenon.

BRIEF DESCRIPTION OF THE INVENTION

The present invention relates to a process for the oligomerization of an olefinic feedstock, comprising:

a) a step of oligomerization of the olefinic feedstock, carried out at a temperature of between 30° C. and 200° C. and a pressure of between 0.1 and 10 MPa, in the presence of a homogeneous catalytic oligomerization system and of a solvent, in a reaction section comprising:

an oligomerization reactor with zones of variable diameter and comprising a liquid phase, and at least one recirculation loop allowing the cooling of at least a part of a liquid-phase fraction to a temperature $T_{loop}$, b) a step of separating a reaction effluent resulting from the oligomerization step a), in a separation section so as to obtain a solvent fraction, c) a step of cooling the solvent fraction resulting from step b) to a temperature below the temperature $T_{loop}$ to which the liquid-phase fraction is cooled in the recirculation loop(s), d) a step of introducing, into the reaction section of the oligomerization step a), the cooled solvent fraction resulting from step c).

Preferably, said reactor with zones of variable diameter comprises n consecutive zones, n being a positive integer of between 2 and 10, with:

for each of the n zones having a diameter Dn which decreases in the direction of the bottom zone to the top zone of said reactor, a ratio (Dn/Dn−1) of the diameter of the upper zone, denoted Dn, to the diameter of the adjacent lower zone, denoted Dn−1, of less than or equal to 0.9, for a given zone, a ratio of the volume of said zone, denoted Vn, to the total volume of the reaction chamber, denoted Vtot, of between 0.2 and 0.8.

Preferably, the n consecutive zones of the reactor with zones of variable diameter are arranged in series along the vertical axis of the reactor so as to define zones in the reaction enclosure having diameters decreasing from the bottom to the top.

Preferably, the solvent fraction resulting from step b) is cooled in step c) to a temperature of between 0° ° C. and 150° C.

Preferably, the solvent fraction resulting from step b) is cooled in step c) to a temperature at least 40° C. lower relative to the temperature $T_{loop}$ of the liquid fraction cooled in the recirculation loop(s).

Preferably, the cooling of the solvent fraction in step c) is carried out by one or more thermal exchangers, preferably chosen from one or more heat exchangers of process fluid/process fluid type, of air cooler type, of cooling water exchanger type.

Preferably, the separation section comprises at least two distillation columns, preferably at least three distillation columns, preferably at least four distillation columns.

Preferably, step d) of introducing the cooled solvent fraction is carried out in the reactor and/or in one or more of the recirculation loops.

Preferably, step d) of introducing at least a part of the cooled solvent fraction is carried out in a recirculation loop upstream or downstream of a thermal exchanger of the recirculation loop(s), preferably downstream of said thermal exchanger.

Preferably, the cooled solvent fraction has a flow rate, as a weight percentage relative to the flow rate of the liquid-phase fraction circulating in the circulation loop(s), of between 0.05% and 15.0%, preferably between 0.1% and 10.0%.

Preferably, the olefinic feedstock comprises olefins having between 2 and 6 carbon atoms, preferably between 2 and 4 carbon atoms.

Preferably, the oligomerization step a) comprises at least one of the following substeps:

- step a1) of introducing the catalytic system,
- step a2) of bringing into contact with olefinic feedstock,
- substep a3) of withdrawing a liquid-phase fraction from the oligomerization reactor,
- substep a4) of cooling at least a part of the liquid-phase fraction withdrawn in step a3) in at least one recirculation loop, to a temperature $T_{loop}$,
- step a5) of introducing the cooled liquid fraction into the reactor.

Preferably, the cooling substep a4) is carried out by circulating at least a part of the liquid-phase fraction withdrawn in substep a3) through one or more thermal exchangers located in the recirculation loop(s).

Preferably, the thermal exchanger(s) used in substep a4) reduce(s) the temperature of the liquid-phase fraction withdrawn in substep a3) by 1.0° C. to 30.0° C., preferably between 2.0° C. and 25.0° C.

Preferably, the reaction effluent is obtained by dividing the liquid fraction withdrawn in substep a3) into two streams.

Definition

In the context of the present invention, the term “separation section” denotes the device(s) for separation, notably by distillation, arranged downstream of the reaction section, with a single device or a plurality of devices arranged in series and/or in parallel, which devices may be identical or different in their sizing or their design/operation.

In the context of the present invention, the terms “upstream” and “downstream” are understood as a function of the general direction of flow of the reaction fluid in the production unit.

In the context of the present invention, the expressions heat exchanger and thermal exchanger are used in an equivalent manner.

A homogeneous catalyst or catalytic system is understood to mean the fact that the catalyst or catalytic system is in the same phase as the reactants and the products of the oligomerization reaction.

Breakthrough is understood to mean the passage of gaseous olefinic feedstock, preferably gaseous ethylene, from the liquid phase to the gas phase in a gas/liquid reactor.

The content of solvent is understood to mean the weight ratio of the total flow rate of solvent injected to the sum of the total flow rate of the gaseous olefinic feedstock, preferably gaseous ethylene, injected and the flow rate of solvent introduced into the reactor.

The term “two-phase gas/liquid reactor” means a reactor comprising a liquid phase and a gas phase, the liquid phase comprising the olefinic feedstock, preferably in gaseous form, in particular gaseous ethylene, the reaction products such as the desired linear α-olefin (i.e. but-1-ene, hex-1-ene, oct-1-ene or the mixture of linear α-olefins), preferably in liquid form, the catalytic system, preferably in liquid form, and a solvent, and a gaseous phase located in the part located at the top of the reactor.

In the context of the present invention, the term “reaction section” denotes a device comprising, preferably consisting of, an oligomerization reactor with zones of variable diameter and one or more recirculation loop(s).

Bottom or lower part of the reaction chamber or of the reactor is understood to mean the lower quarter of the reaction chamber or of the reactor.

Top of the reaction chamber or of the reactor is understood to mean the upper quarter of the reaction chamber or of the reactor.

Bottom zone is understood to mean the first zone according to the invention located in the lower part of the reaction chamber or of the reactor, at the level of the bottom of said chamber or of the reactor.

Top zone is understood to mean the final zone according to the invention located in the upper part of the reaction chamber or of the reactor at the level of the top of said chamber or of the reactor.

Degree of saturation is understood to mean the percentage of olefinic feedstock, preferably of ethylene, dissolved in the liquid phase with respect to the maximum amount of gaseous olefinic feedstock, preferably of ethylene, which might be dissolved in said liquid phase, defined by the thermodynamic equilibrium between the partial pressure of gaseous olefinic feedstock, preferably of gaseous ethylene, and said liquid phase. The degree of saturation can be measured by gas chromatography.

The upper part of the reactor is understood to mean the upper quarter of said reactor containing the liquid phase.

Volume of reaction liquid is understood to mean the amount by volume of liquid phase contained in the reactor and/or the recirculation loop(s) and in which the oligomerization reaction takes place.

The volume of a recirculation loop or recirculation loops denotes the size of said loop(s) corresponding to the volume of reaction liquid which may be contained by said loop(s).

DETAILED DESCRIPTION

For the purposes of the present invention, the various embodiments presented may be used alone or in combination with each other, without any limit to the combinations.

For the purposes of the present invention, the various ranges of parameters for a given step, such as the pressure ranges and the temperature ranges, may be used alone or in combination. For example, for the purposes of the present invention, a preferred range of pressure values can be combined with a more preferred range of temperature values.

Process

The present invention relates to a process for the oligomerization of an olefinic feedstock carried out in a reactor with zones of variable diameter and in which a solvent fraction resulting from a downstream separation step is cooled and recycled to the reaction section so as to partly control the exothermicity of the oligomerization reaction.

In particular, the present invention relates to a process for the oligomerization of an olefinic feedstock, comprising:

a) a step of oligomerization of the olefinic feedstock, carried out at a temperature of between 30° C. and 200° ° C. and a pressure of between 0.1 and 10 MPa, in the presence of a homogeneous catalytic oligomerization system and of a solvent, in a reaction section comprising:

an oligomerization reactor with zones of variable diameter and comprising a liquid phase, and at least one recirculation loop allowing the cooling of at least a part of a liquid-phase fraction to a temperature $T_{loop}$, b) a step of separating a reaction effluent resulting from the oligomerization step a), in a separation section so as to obtain a solvent fraction, c) a step of cooling the solvent fraction resulting from step b) to a temperature below the temperature $T_{loop}$ to which the liquid-phase fraction is cooled in the recirculation loop(s), d) a step of introducing, into the reaction section of the oligomerization step a), the cooled solvent fraction resulting from step c).

The invention makes it possible to reduce the temperature difference between the liquid-phase fraction withdrawn and the fluid used for the heat exchange at the level of the recirculation loop(s), while minimizing the temperature of the solvent introduced into the reactor with zones of variable diameter by the recirculation loop(s) and while maximizing the volume of reaction liquid in the reactor, thereby making it possible to improve the saturation, of said liquid, with gaseous olefinic feedstock. The control of the temperature by introduction into the reaction section of the cooled solvent fraction resulting from the downstream separation makes it possible to reduce the amount of heat to be exchanged in the recirculation loops and therefore makes it possible to reduce the size of the exchangers. The saving regarding the surface area of exchange of the thermal exchangers of the recirculation loop(s) may advantageously be of the order of 1% to 50%, preferably between 2% and 40% and preferentially between 3% and 30% over the exchange surface area.

Furthermore, the oligomerization reaction takes place both in the reaction liquid contained in the reactor and in the recirculation loop(s). The reduction of the size of the heat exchangers means that the volume of at least one recirculation loop decreases. In the process according to the invention, the volume of reaction liquid in the reactor is increased compared to a process not implementing the invention, at an identical volume of total reaction liquid (reactor+recirculation loop), thereby making it possible to improve the saturation of the liquid reaction medium with olefinic feedstock and therefore the performance of the process.

In the process according to the invention, the volume proportion of reaction liquid in a recirculation loop relative to the total volume of reaction liquid decreases compared to a process not implementing the invention, at an identical amount of reaction liquid in the reactor. This reduction, and in particular combined with the use of the reactor with zones of variable diameter, makes it possible to reduce the residence time and therefore to improve the performance of the catalytic system in terms of activity and selectivity, while improving the saturation of the liquid with olefinic feedstock Thus, the present invention makes it possible to easily adjust the productivity and profitability of the oligomerization process as a function of the performance of the catalytic system used.

Homogeneous Catalytic Oligomerization System

All the catalytic systems known to those skilled in the art and capable of being employed in dimerization, trimerization or tetramerization processes and more generally in the oligomerization processes according to the invention come within the field of the invention. Said catalytic systems and also the implementation thereof are notably described in applications FR 2 984 311, FR 2 552 079, FR 3 019 064, FR 3 023 183, FR 3 042 989 or else in application FR 3 045 414.

Preferably, the catalytic systems comprise, and preferably consist of:

a metal precursor, preferably based on nickel, titanium or chromium, optionally an activating agent, optionally an additive, and optionally a solvent.

The Metal Precursor

The metal precursor used in the catalytic system is chosen from compounds based on nickel, titanium or chromium.

In one embodiment, the metal precursor is based on nickel and preferentially comprises nickel in (+II) oxidation state. Preferably, the nickel precursor is chosen from nickel(II) carboxylates, for instance nickel 2-ethylhexanoate, nickel (II) phenates, nickel(II) naphthenates, nickel(II) acetate, nickel(II) trifluoroacetate, nickel(II) triflate, nickel(II) acetylacetonate, nickel(II) hexafluoroacetylacetonate, π-allylnickel(II) chloride, π-allylnickel(II) bromide, methallylnickel(II) chloride dimer, $\eta^3$-allylnickel(II) hexafluorophosphate, $\eta^3$-methallylnickel(II) hexafluorophosphate and nickel(II) 1,5-cyclooctadienyl, in their hydrated or non-hydrated form, taken alone or as a mixture.

In a second embodiment, the metal precursor is based on titanium and preferentially comprises a titanium aryloxy or alkoxy compound.

The titanium alkoxy compound advantageously corresponds to the general formula $[Ti(OR)_4]$ in which R is a linear or branched alkyl radical. Among the preferred alkoxy radicals, non-limiting examples which may be mentioned include tetraethoxy, tetraisopropoxy, tetra(n-butoxy) and tetra(2-ethylhexyloxy).

The titanium aryloxy compound advantageously corresponds to the general formula $[Ti(OR')_4]$ in which R' is an aryl radical which is unsubstituted or substituted with alkyl or aryl groups. The radical R' may include heteroatom-based substituents. The preferred aryloxy radicals are chosen from phenoxy, 2-methylphenoxy, 2,6-dimethylphenoxy, 2,4,6-trimethylphenoxy, 4-methylphenoxy, 2-phenylphenoxy, 2,6-diphenylphenoxy, 2,4,6-triphenylphenoxy, 4-phenylphenoxy, 2-(tert-butyl)-6-phenylphenoxy, 2,4-di(tert-butyl)-6-phenylphenoxy, 2,6-diisopropylphenoxy, 2,6-di(tert-butyl) phenoxy, 4-methyl-2,6-di(tert-butyl)phenoxy, 2,6-dichloro- 4-(tert-butyl)phenoxy and 2,6-dibromo-4-(tert-butyl) phenoxy, the biphenoxy radical, binaphthoxy and 1,8-naphthalenedioxy.

According to a third embodiment, the metal precursor is based on chromium and preferentially comprises a chromium(II) salt, a chromium(III) salt or a salt of different oxidation state which may include one or more identical or different anions, for instance halides, carboxylates, acetylacetonates or alkoxy or aryloxy anions. Preferably, the chromium-based precursor is chosen from $CrCl_3$, $CrCl_3$(tetrahydrofuran)$_3$, Cr(acetylacetonate)$_3$, Cr(naphthenate)$_3$, Cr(2-ethylhexanoate)$_3$ and Cr(acetate)$_3$.

The concentration of nickel, titanium or chromium is between 0.001 and 300.0 ppm by weight of atomic metal, relative to the reaction weight, preferably between 0.002 and 100.0 ppm, preferentially between 0.003 and 50.0 ppm, more preferentially between 0.05 and 20.0 ppm and even more preferentially between 0.1 and 10.0 ppm by weight of atomic metal, relative to the liquid reaction weight, that is to say the weight of liquid phase contained in the reactor and/or the recirculation loop(s).

The Activating Agent

Optionally, irrespective of the metal precursor, the catalytic system comprises one or more activating agents chosen from aluminium-based compounds, such as methylaluminium dichloride ($MeAlClI_2$), dichloroethylaluminum ($EtAlClI_2$), ethylaluminum sesquichloride ($Et_3Al_2Cl_3$), chlorodiethylaluminum ($Et_2AlCl$), chlorodiisobutylaluminum ($i\text{-}Bu_2AlCl$), triethylaluminum ($AlEt_3$), tripropylaluminum ($Al(n\text{-}Pr)_3$), triisobutylaluminum ($Al(i\text{-}Bu)_3$), diethylethoxyaluminum ($Et_2AlOEt$), methylaluminoxane (MAO), ethylaluminoxane and modified methylaluminoxanes (MMAO).

The Additive

Optionally, the catalytic system comprises one or more additives.

The additive is chosen from monodentate phosphorus-based compounds, bidentate phosphorus-based compounds, tridentate phosphorus-based compounds, olefinic compounds, aromatic compounds, nitrogenous compounds, bipyridines, diimines, monodentate ethers, bidentate ethers, monodentate thioethers, bidentate thioethers, monodentate or bidentate carbenes, mixed ligands such as phosphinopyridines, iminopyridines, bis(imino)pyridines.

When the metal precursor of the catalytic system is nickel-based, the additive is chosen from compounds of nitrogenous type, such as trimethylamine, triethylamine, pyrrole, 2,5-dimethylpyrrole, pyridine, 2-methylpyridine, 3-methylpyridine, 4-methylpyridine, 2-methoxypyridine, 3-methoxypyridine, 4-methoxypyridine, 2-fluoropyridine, 3-fluoropyridine, 3-trifluoromethylpyridine, 2-phenylpyridine, 3-phenylpyridine, 2-benzylpyridine, 3,5-dimethylpyridine, 2,6-di(tert-butyl)pyridine and 2,6-diphenylpyridine, quinoline, 1,10-phenanthroline, N-methylpyrrole, N-butylpyrrole, N-methylimidazole, N-butylimidazole, 2,2'-bipyridine, N, N'-dimethylethane-1,2-dimine, N,N'-di(t-butyl)ethane-1,2-diimine, N, N'-di(t-butyl)butane-2,3-diimine, N, N'-diphenylethane-1,2-diimine, N, N'-bis(2,6-dimethylphenyl)ethane-1,2-diimine, N, N'-bis(2,6-diisopropylphenyl)ethane-1,2-dimine, N,N'-diphenylbutane-2,3-diimine, N,N'-bis(2,6-dimethylphenyl)butane-2,3-diimine or N,N'-bis(2,6-diisopropylphenyl)butane-2,3-diimine, or compounds of phosphine type independently chosen from tributylphosphine, triisopropylphosphine, tricyclopentylphosphine, tricyclohexylphosphine, triphenylphosphine, tris(o-tolyl)phosphine, bis(diphenylphosphino) ethane, trioctylphosphine oxide, triphenylphosphine oxide or triphenyl phosphite, or compounds corresponding to the general formula (I) or one of the tautomers of said compound:

(I)

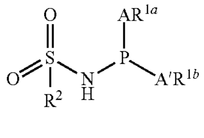

in which:

A and A', which may be identical or different, are independently an oxygen or a single bond between the phosphorus atom and a carbon atom, the groups $R^{1a}$ and $R^{1b}$ are independently chosen from methyl, trifluoromethyl, ethyl, n-propyl, isopropyl, n-butyl, isobutyl, t-butyl, pentyl, cyclohexyl and adamantyl groups, which may or may not be substituted and may or may not contain heteroelements; phenyl, o-tolyl, m-tolyl, p-tolyl, mesityl, 3,5-dimethylphenyl, 4-(n-butyl)phenyl, 2-methylphenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-bis(tert-butyl)-4-methoxyphenyl, 4-chlorophenyl, 3,5-bis(trifluoromethyl)phenyl, benzyl, naphthyl, bisnaphthyl, pyridyl, bisphenyl, furyl and thiophenyl groups, the group $R^2$ is independently chosen from methyl, trifluoromethyl, ethyl, n-propyl, isopropyl, n-butyl, isobutyl, t-butyl, pentyl, cyclohexyl and adamantyl groups, which may or may not be substituted and may or may not contain heteroelements; phenyl, o-tolyl, m-tolyl, p-tolyl, mesityl, 3,5-dimethylphenyl, 4-(n-butyl)phenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-di(tert-butyl)-4-methoxyphenyl, 4-chlorophenyl, 3,5-bis(trifluoromethyl)phenyl, benzyl, naphthyl, bisnaphthyl, pyridyl, bisphenyl, furyl and thiophenyl groups.

When the metal precursor of the catalytic system is based on titanium, the additive is chosen from diethyl ether, diisopropyl ether, dibutyl ether, diphenyl ether, 2-methoxy-2-methylpropane, 2-methoxy-2-methylbutane, 2,2-dimethoxypropane, 2,2-bis(2-ethylhexyloxy)propane, 2,5-dihydrofuran, tetrahydrofuran, 2-methoxytetrahydrofuran, 2-methyltetrahydrofuran, 3-methyltetrahydrofuran, 2,3-dihydropyran, tetrahydropyran, 1,3-dioxolane, 1,3-dioxane, 1,4-dioxane, dimethoxyethane, bis(2-methoxyethyl) ether, benzofuran, glyme and diglyme, taken alone or as a mixture.

When the metal precursor of the catalytic system is based on chromium, the additive is chosen from:

compounds of nitrogenous type, such as trimethylamine, triethylamine, pyrrole, 2,5-dimethylpyrrole, pyridine, 2-methylpyridine, 3-methylpyridine, 4-methylpyridine, 2-methoxypyridine, 3-methoxypyridine, 4-methoxypyridine, 2-fluoropyridine, 3-fluoropyridine, 3-trifluoromethylpyridine, 2-phenylpyridine, 3-phenylpyridine, 2-benzylpyridine, 3,5-dimethylpyridine, 2,6-di(tert-butyl)pyridine and 2,6-diphenylpyridine, quinoline, 1,10-phenanthroline, N-methylpyrrole, N-butylpyrrole, N-methylimidazole, N-butylimidazole, 2,2'-bipyridine, N, N'-dimethylethane-1,2-diimine, N,N'-di(t-butyl)ethane-1,2-diimine, N, N'-di(t-butyl)butane-2,3-diimine, N,N'-diphenylethane-1,2-diimine, N, N'-bis(2,6-dimethylphenyl)ethane-1,2-diimine, N,N'-bis(2,6-diisopropylphenyl)ethane-1,2-diimine, N,N'-diphenylbutane-2,3-diimine, N,N'-bis(2,6-dimethylphenyl)butane-2,3-diimine or N,N'-bis(2,6-diisopropylphenyl)butane-2,3-diimine, or aryloxy compounds of general formula $[M(R^3O)_{2-n}X_n]_y$, in which:

M is chosen from magnesium, calcium, strontium and barium, preferably magnesium, $R^3$ is an aryl radical containing from 6 to 30 carbon atoms and X is a halogen or an alkyl radical containing from 1 to 20 carbon atoms, n is an integer which can take the values of 0 or 1, and y is an integer between 1 and 10; preferably, y is equal to 1, 2, 3 or 4.

Preferably, the aryloxy radical $R^3O$ is chosen from 4-phenylphenoxy, 2-phenylphenoxy, 2,6-diphenylphenoxy, 2,4,6-triphenylphenoxy, 2,3,5,6-tetraphenylphenoxy, 2-(tert-butyl)-6-phenylphenoxy, 2,4-di(tert-butyl)-6-phenylphenoxy, 2,6-diisopropylphenoxy, 2,6-dimethylphenoxy, 2,6-di(tert-butyl)phenoxy, 4-methyl-2,6-di(tert-butyl)phenoxy, 2,6-dichloro-4-(tert-butyl)phenoxy and 2,6-dibromo-4-(tert-butyl)phenoxy. The two aryloxy radicals may be borne by the same molecule, for instance the biphenoxy radical, binaphthoxy or 1,8-naphthalenedioxy. Preferably, the aryloxy radical $R^3O$ is 2,6-diphenylphenoxy, 2-(tert-butyl)-6-phenylphenoxy or 2,4-di(tert-butyl)-6-phenylphenoxy.

Oligomerization Step a)

The process according to the invention therefore comprises a step a) of oligomerization of an olefinic feedstock carried out at a temperature between 30° C. and 200° C. and a pressure between 0.1 and 10 MPa, in the presence of a homogeneous catalytic oligomerization system and a solvent. Said oligomerization step a) is carried out in a reaction section comprising an oligomerization reactor with zones of variable diameter and at least one recirculation loop enabling the control of the temperature in said reactor via the cooling of a liquid-phase fraction. The cooling of the liquid fraction consists in cooling said fraction to a temperature below the oligomerization temperature (that is to say that of the liquid phase in the reactor) so as to control the exothermicity of the reaction.

Preferably, the reactor with zones of variable diameter used in the process according to the invention comprises n consecutive zones, n being a positive integer between 2 and 10, with:

for each of the n zones a diameter Dn which decreases in the direction of the bottom zone to the top zone of said reactor, a ratio (Dn/Dn−1) of the diameter of the upper zone, denoted Dn, to the diameter of the adjacent lower zone, denoted Dn−1, of less than or equal to 0.9, for a given zone, a ratio of the volume of said zone, denoted Vn, to the total volume of the reaction chamber, denoted Vtot, of between 0.2 and 0.8.

The use of a reactor with zones of variable diameter according to the present invention makes it possible to increase the total height of the reactor and therefore the height of the liquid phase, without modifying the volume of the reactor or of the liquid phase used in an oligomerization reaction, which has the effect of improving the dissolution of the gaseous olefinic feedstock, in particular of the gaseous ethylene, and therefore of limiting the phenomenon of breakthrough for a given volume of liquid phase, and therefore to improve the productivity of the process. Thus, the reactor with zones of variable diameter makes it possible, for a given volume of liquid phase, to increase the height of the liquid phase compared to a constant-diameter reactor.

Advantageously, the use of the reactor with zones of variable diameter according to the invention in an oligomerization process, preferably using a homogeneous catalyst, makes it possible to have a degree of saturation with olefinic feedstock, in particular with ethylene, dissolved in the liquid phase of greater than 70.0%, preferably between 70.0% and 100%, preferably between 80.0% and 100%, preferably between 80.0% and 99.0%, preferably between 85.0% and 99.0% and even more preferably between 90.0% and 98.0%.

The degree of saturation with dissolved olefinic feedstock, in particular with dissolved ethylene, can be measured by any method known to those skilled in the art, for example by gas chromatography (commonly referred to as GC) analysis of a liquid-phase fraction withdrawn from the reactor.

The process using the reactor with zones of variable diameter according to the invention makes it possible to obtain linear olefins and in particular linear α-olefins by bringing olefin(s) and a catalytic system into contact, optionally in the presence of an additive and/or of a solvent, and by the use of said gas/liquid reactor with zones of variable diameter.

The n consecutive zones of the reactor used in the process according to the invention are placed in series along the vertical axis of the reactor so as to define reaction zones having diameters that decrease from the bottom to the top of the reactor and thus to increase the height of the liquid phase which may be contained in the reactor according to the invention compared to the height of a constant-diameter reactor, and thus to increase the time during which the olefinic feedstock is present in the liquid phase so as to promote its dissolution.

Advantageously, for a given reactor volume and thus a given liquid volume, the n consecutive zones of decreasing diameter in said reactor make it possible to increase the height of the liquid which may be contained in said reactor and thus the residence time of the gaseous olefinic feedstock introduced into said liquid phase. Thus, the present invention makes it possible to increase the amount of olefinic feedstock, preferably of ethylene, dissolved in the liquid phase and thus to limit the breakthrough phenomenon.

Preferably, the reactor comprises a number n of zones of between 2 and 10, preferably between 2 and 8, preferably between 2 and 6, preferably between 2 and 5, and very preferably n is preferably equal to 2, 3, 4 or 5.

The ratio (Dn/Dn−1) of the diameter of an upper zone n, denoted Dn, to the diameter of the adjacent lower zone n−1, denoted Dn−1, is less than or equal to 0.9. Preferably, the ratio Dn/Dn−1 is between 0.1 and 0.9, preferably between 0.15 and 0.85, preferably between 0.2 and 0.8 and preferably between 0.25 and 0.75 and very preferably between 0.3 and 0.7.

The n zones making up the reactor have a total height, denoted Htot, the sum of which is equal to the total height of the reactor.

Advantageously, the ratio (Hn/Hn−1) of the height of an upper zone n, denoted Hn, to the height of the adjacent lower zone n−1, denoted Hn−1, is between 0.2 and 3.0, preferably between 0.3 and 2.5, preferably between 0.4 and 2.0, preferably between 0.5 and 1.5 and preferably between 0.6 and 1.0.

Preferably, for a given zone, the ratio of the volume, denoted Vn, to the total volume, denoted Vtot (said ratio being denoted Vn/Vtot), of the reactor corresponding to the sum of the n zones is between 0.2 and 0.8. Preferably, said ratio (Vn/Vtot) is between 0.25 and 0.75, preferably between 0.3 and 0.7 and preferably between 0.35 and 0.65.

Preferably, the reactor is cylindrical in shape and has a ratio of the total height to the diameter of the bottom zone of said reactor (denoted Htot/D1) of between 1 and 17, preferably between 1 and 8 and preferably between 2 and 7.

In a first particular embodiment represented in FIG. 2 or FIG. 3, the n zones making up the reactor according to the invention are formed by cylinders of decreasing diameter. Said cylinders are connected to one another by means of walls perpendicular to the vertical axis or having an angle $\alpha$ of between 90 and 160° with the vertical axis, represented in FIG. 2, so as to facilitate and especially not to block the rise of the gaseous ethylene bubbles in the liquid phase. Preferably, said angle is between 95 and 145° and preferably between 100 and 130°.

In a second particular embodiment represented in FIG. 4, the n zones making up the reactor according to the invention are formed by internals positioned inside the reactor so as to reduce its diameter over a given zone. Said internals may for example be solid metal walls.

Advantageously, regardless of the embodiment, the securing of the elements constituting the reactor is carried out by attaching the cylinders and/or the internals, for example by welding, by adhesive bonding, by screwing or by bolting, alone or in combination, or any other similar means. Preferably, the attaching is carried out by welding.

Preferably, the oligomerization reactor is chosen from a two-phase gas/liquid reactor, preferably a bubble column type reactor.

The olefinic feedstock preferably comprises olefins having between 2 and 6 carbon atoms, preferably between 2 and 4 carbon atoms. Preferably, the olefinic feedstock is chosen from butene, more particularly isobutene or but-1-ene, propylene and ethylene, alone or as a mixture.

In the remainder of the present text, unless otherwise indicated, when ethylene is mentioned specifically, this also denotes olefins having between 2 and 6 carbon atoms, such as for example isobutene or but-1-ene, propylene, and ethylene.

Preferably, the oligomerization process is a process for dimerization, trimerization or tetramerization, of the olefinic feedstock, preferably of ethylene.

Advantageously, the oligomerization process is performed at a pressure of between 0.1 and 10.0 MPa, preferably between 0.2 and 9.0 MPa and preferentially between 0.3 and 8.0 MPa, at a temperature between 30° C. and 200° C., preferably between 35° C. and 180° C., preferably between 45° C. and 170° C., preferentially between 60° C. and 160° C., preferably between 70° C. and 150° C., preferably between 80° C. and 145° C. and preferably between 100° C. and 140° C.

The reaction effluent resulting from step a) which is sent to the separation section downstream of the reaction section is obtained by withdrawing a liquid fraction from the reactor. In particular, the reaction effluent resulting from step a) which is sent to the separation section downstream of the reaction section corresponds to at least a part of a liquid-phase fraction, withdrawn from the oligomerization reactor with zones of variable diameter. Advantageously, the flow rate of the reaction effluent is regulated in order to maintain a constant liquid level in the reactor.

Since the oligomerization reaction takes place both in the reactor and in the recirculation loop(s), the residence time in the reaction section is therefore understood over the whole of the volume of the reactor and of the recirculation loop(s) forming the reaction section.

Advantageously, the oligomerization process is performed with a solvent content of between 0 and 90 wt %, preferably between 10 and 85 wt %, preferably between 20 and 80 wt %, preferably between 30 and 75 wt %. According to one preferred embodiment of the invention, the oligomerization process is performed in a two-phase gas/liquid reactor of bubble column type with a gaseous olefinic feedstock, for example with a gaseous ethylene feedstock. The dissolving of the bubbles of olefinic feedstock, in particular of ethylene, in the reaction medium takes place in the bubble column. The higher the height of liquid available in this column, the closer the dissolution of ethylene is to complete saturation. Since the selectivity of the reaction towards the main reaction product is inversely related to the conversion of the olefinic feedstock, preferably of the ethylene, in the liquid, maximizing the amount of dissolved olefinic feedstock will make it possible, at constant olefinic feedstock flow rate at the inlet of the reactor, to reduce the conversion and therefore to increase the selectivity.

Since the recirculation loops represent a significant proportion of the volume of reaction liquid of the reaction section, it is advantageous to reduce this volume as much as possible in order:

- either to increase the volume of reaction liquid in the reactor (for example in a bubble column) and consequently to increase the height of the liquid phase in the reactor, to maximize the saturation with ethylene in the liquid, in a synergistic manner with the reactor with zones of variable diameter,
- or to decrease the volume of the recirculation loop(s) while maintaining a constant volume of the reactor and thus to reduce the residence time, which may make it possible to improve the performance of the catalytic system in terms of activity and selectivity.

The solvent(s) are advantageously chosen from ethers, alcohols, halogenated solvents and hydrocarbons, which may be saturated or unsaturated, cyclic or non-cyclic, aromatic or non-aromatic, comprising between 1 and 20 carbon atoms, preferably between 4 and 15 carbon atoms, preferentially between 4 and 12 carbon atoms and even more preferentially between 4 and 8 carbon atoms.

Preferably, the solvent is chosen from pentane, hexane, cyclohexane, methylcyclohexane, heptane, butane or isobutane, cycloocta-1,5-diene, benzene, toluene, ortho-xylene, mesitylene, ethylbenzene, diethyl ether, tetrahydrofuran, 1,4-dioxane, dichloromethane, dichloroethane, tetrachloroethane, hexachloroethane, chlorobenzene, dichlorobenzene, butene, hexene and octene, pure or as a mixture.

Preferably, the solvent may be advantageously chosen from the products of the oligomerization reaction. Preferably, the solvent used is cyclohexane.

In order to discharge the energy of the reaction, one or more recirculation loops are used. The recirculation loop makes it possible to circulate, from the bottom of the reactor, a liquid-phase fraction comprising the products of the reaction, the solvent and the catalytic system, through an exchanger before being sent to the top of the reactor.

Preferably, the linear $\alpha$-olefins obtained comprise from 4 to 20 carbon atoms, preferably from 4 to 18 carbon atoms, preferably from 4 to 10 carbon atoms and preferably from 4 to 8 carbon atoms. Preferably, the olefins are linear $\alpha$-olefins chosen from but-1-ene, hex-1-ene and oct-1-ene.

Advantageously, the reaction section comprises one or more reactors of the gas/liquid or all-liquid type, at least one of the reactors of which has zones of variable diameter, arranged in series and/or in parallel, and also their associated equipment such as:

one or more recirculation loop(s) comprising one or more thermal exchangers and associated with (each of) the reactor(s) to control the exothermicity of the reaction, means for introducing the catalytic oligomerization system into the reaction section(s), means external to the reaction section for separating/neutralizing the catalytic system.

Advantageously, the oligomerization step a) comprises at least one of the following substeps:

step a1) of introducing the catalytic system, step a2) of bringing into contact with olefinic feedstock, step a3) of withdrawing a liquid-phase fraction, step a4) of cooling at least a part of the fraction of of the liquid fraction, step a5) of introducing the cooled liquid fraction into the reactor.

Preferably, the oligomerization step a) comprises the substeps a1), a2), a3), a4) and a5).

In one particular embodiment, the reaction effluent resulting from step a), and which is advantageously sent to the downstream separation section of the reaction section, is obtained by dividing the liquid fraction withdrawn at step a3) into two streams. The first stream is sent to the cooling step d), and the second stream corresponds to the reaction effluent and is sent to the downstream separation section. Advantageously, the flow rate of the reaction effluent is regulated in order to maintain a constant liquid level in the reactor. Preferably, the flow rate of said reaction effluent is from 5 to 200 times lower than the liquid flow rate sent to the cooling step a4) (that is to say the flow rate of the part of the liquid-phase fraction sent to step a4). Preferably, the flow rate of said reaction effluent is 5 to 150 times lower, preferably 10 to 120 times lower and more preferably 20 to 100 times lower than the liquid flow sent to the cooling step a4).

Step a1) of Introducing the Catalytic System

Advantageously, the oligomerization step a) comprises a substep a1) of introducing a catalytic system comprising a metal precursor and advantageously an activating agent, optionally an additive and optionally a solvent or mixture of solvents.

Preferably, the catalytic system is introduced as a mixture with the cooled liquid fraction introduced into the reactor in step a5).

Preferably, the pressure for introduction into the reactor is between 0.1 and 10.0 MPa, preferably between 0.2 and 9.0 MPa and preferentially between 0.3 and 8.0 MPa.

Step a2) of Bringing into Contact with the Olefinic Feedstock

Advantageously, the oligomerization step a) comprises a substep a2) of introducing the advantageously gaseous olefinic feedstock, preferably gaseous ethylene. Preferably, said olefinic feedstock is introduced into the liquid phase in the lower part of the reactor. The olefinic feedstock may comprise fresh feedstock, and preferably, as a mixture with the olefinic feedstock recycled from a downstream separation step to the oligomerization step a).

Preferably, when the olefinic feedstock introduced is gaseous, said feedstock is distributed by dispersion during its introduction into the lower liquid phase of the reactor by a means capable of carrying out said dispersion uniformly over the entire section of the reactor. Preferably, the dispersion means is chosen from a distributing system with a homogeneous distribution of the points for injection of the olefinic feedstock over the entire section of the reactor.

Preferably, the olefinic feedstock is introduced at a flow rate of between 1 and 250 t/h, preferably between 2 and 200 t/h, preferably between 5 and 100 t/h.

Preferably, the flow rate of olefinic feedstock introduced in step a2) is controlled by the pressure in the reactor.

According to a specific implementation of the invention, a stream of gaseous hydrogen can also be introduced into the reactor, with a flow rate representing from 0.01% to 1.0% by weight of the flow rate of incoming olefinic feedstock. Preferably, the stream of gaseous hydrogen is introduced by the pipe employed for the introduction of the olefinic feedstock.

Step a3) of Withdrawing a Liquid-Phase Fraction

Advantageously, the oligomerization step a) comprises a substep a3) of withdrawing a liquid-phase fraction from the oligomerization reactor, preferably in the lower part of said reactor.

The withdrawal implemented in step a3) is preferably carried out below the level of injection of the olefinic feedstock, and preferably in the bottom of the chamber. The withdrawal is carried out by any means capable of carrying out the withdrawal and preferably by means of a pipe combined with a pump.

Preferably, the withdrawal flow rate is between 10 and 10 000 t/h and preferably between 100 and 7000 t/h.

Step a4) of Cooling the Liquid Fraction

Advantageously, the oligomerization step a) comprises a substep a4) of cooling at least a part of the liquid-phase fraction withdrawn in step a3) at a temperature T(loop). Preferably, the cooling step is carried out by circulating at least a part of the liquid-phase fraction withdrawn in step a3) through one or more thermal exchangers located in the recirculation loop.

Advantageously, the heat exchanger(s) used in substep a4) make it possible to reduce the temperature of the liquid-phase fraction by 1.0° C. to 30.0° C., preferably between 2.0° C. and 25° C., preferably between 3.0° ° C. and 20.0° C. and preferably between 5.0° C. and 15.0° C. Advantageously, the cooling of the liquid fraction makes it possible to maintain the temperature of the reaction medium within the desired temperature ranges for carrying out the oligomerization reaction within the reactor.

Advantageously, the implementation of the step of cooling the liquid via the recirculation loop also makes it possible to carry out the stirring of the reaction medium and thus to homogenize the concentrations of the reactive entities throughout the liquid volume of the reactor.

Step a5) of Introducing the Cooled Liquid Fraction

Advantageously, the oligomerization step a) comprises a substep a5) of introducing the cooled liquid fraction resulting from step a4).

The introduction of the cooled liquid fraction resulting from step a4) is preferably carried out in the liquid phase of the reactor, preferably in the upper part of said reactor, by any means known to those skilled in the art, such as a pipe.

Preferably, the flow rate for introduction of the cooled liquid fraction is between 10 and 10 000 t/h and preferably between 100 and 7000 t/h.

Substeps a3) to a5) constitute a recirculation loop. Advantageously, the recirculation loop also makes it possible to ensure, in addition to the control of the temperature in the reactor, the stirring of the reaction medium, and thus to homogenize the concentrations of the reactive entities throughout the liquid volume of the reactor.

Downstream Separation Step b)

The process according to the invention therefore comprises a step b) of separation of an effluent resulting from the oligomerization step a) in a separation section so as to obtain, inter alia, a solvent fraction.

Said solvent fraction is mainly composed of solvent. Advantageously, the solvent content of said solvent fraction is greater than or equal to 95 wt %, preferably greater than 98 wt % and preferably greater than or equal to 99 wt %.

Typically, the separation step located downstream of the reaction section may use separation means, such as distillation columns, operating in series and based on the differences in boiling points of the compounds to be separated. The compounds to be separated comprise the product(s) of the oligomerization reaction such as the linear α-olefins obtained, optionally the olefinic feedstock that has not reacted, and the solvent(s).

Preferably, the separation step also includes a preliminary step of neutralizing the catalyst. Thus, the separation step c) can implement a catalyst neutralization section located upstream of the separation section, said neutralization section being advantageously downstream of the reaction section. The catalyst may then be removed from the products of the reaction in a dedicated manner or as a mixture with the heaviest compounds.

Preferably, the separation section comprises at least two distillation columns, preferably at least three distillation columns, preferably at least four distillation columns. Said columns are positioned in parallel and/or in series, preferably in series. According to a preferred variant, the distillation section comprises three distillation columns. The separation of the solvent fraction can be carried out in any one of the distillation columns of the downstream separation section as long as said solvent fraction is mainly composed of solvent in order to be able to recycle said solvent fraction to the oligomerization reactor.

Advantageously, the separation step b) uses a first distillation column at a pressure of between 0.1 and 3.0 MPa, preferably between 0.5 and 1 MPa, a column top temperature of between 0° C. and 100° C., preferably between 40° C. and 80° C., and a column bottom temperature of between 100° C. and 300° C., preferably between 140° C. and 220° C. Said first distillation column makes it possible to separate the unconverted olefinic feedstock, in particular unconverted ethylene, in a top fraction from the rest of the compounds in the bottom fraction.

Advantageously, the separation step b) uses a second distillation column at a pressure of between 0 and 2.0 MPa, preferably between 0.01 and 1.0 MPa, a column top temperature of between 20° C. and 150° C., preferably between 40° C. and 130° C., and a column bottom temperature of between 50° C. and 300° C., preferably between 80° C. and 250° C. Preferably, said second column makes it possible to separate said bottom fraction resulting from the first column into a top fraction comprising the linear α-olefins obtained, in particular hex-1-ene, and the solvent, and a bottom fraction comprising the heaviest compounds.

Advantageously, the separation step b) uses a third distillation column at a pressure of between 0 and 1.0 MPa, preferably between 0.01 and 0.5 MPa, a column top temperature of between 30° C. and 130° C., preferably between 50° C. and 90° C., and a column bottom temperature of between 50° C. and 200° C., preferably between 90° C. and 180° C. Preferably, said third column makes it possible to separate the hex-1-ene at the top from the solvent at the bottom.

By way of non-limiting example, in the case of the trimerization of ethylene to hex-1-ene, the reaction effluent resulting from the ethylene trimerization step a) comprising ethylene, the solvent, the catalytic system for trimerization of the ethylene and the products formed including hex-1-ene, can be separated in a separation step b) comprising at least the following substeps:

b1) a first step of separating, in a first distillation column, the effluent from the ethylene trimerization reaction, into a top fraction comprising the unconverted ethylene and a bottom fraction, b2) a second step of separating, in at least one other distillation column, at least a part of the bottom fraction resulting from step b1) into a top fraction comprising hex-1-ene and the solvent and a bottom fraction comprising C8+ hydrocarbons, b3) a third step of separating, in a final distillation column, at least a part of the fraction comprising hex-1-ene and the solvent resulting from step b2) into a top fraction comprising mainly hex-1-ene and into a bottom fraction comprising mainly the solvent, advantageously at least partly constituting the solvent fraction.

In accordance with the invention, at least one solvent fraction originating from the bottom fraction resulting from step b3) is cooled in step c) then sent back into the reaction section in step d).

Cooling Step c)

The process according to the invention comprises a step c) of cooling the solvent fraction resulting from the downstream separation step b) to a temperature below the temperature $T_{loop}$ to which the liquid-phase fraction is cooled in the recirculation loop(s) of the reaction section.

The cooling of the solvent fraction to a temperature below the temperature $T_{loop}$ of the recirculation loop, preferably from the temperature of the cooled liquid fraction obtained at the end of step a4), makes it possible to reduce the heat exchange, that is to say the amount of heat exchanged, needed in the recirculation loop(s) in order to attain the temperature of the cooled liquid fraction resulting from said loop which is introduced into the reactor, and therefore to reduce the size of the exchanger(s).

The cooling of the solvent fraction in step c) may be carried out by exchange in one or more thermal exchangers either with a process fluid, or with air, or with cooling water or any other type of cold fluid that makes it possible to attain the desired temperature or using a combination of these exchangers. Advantageously, the exchanger is chosen from one or more heat exchangers of process fluid/process fluid type (of TEMA type or other types known to those skilled in the art), of air cooler type, of cooling water exchanger type or any other type of cold fluid that makes it possible to attain the desired temperature.

Advantageously, the solvent fraction resulting from step b) is cooled to a temperature of between 0° C. and 150° C., preferably between 5° C. and 100° C., preferably between 10° C. and 90° C., preferably between 20° C. and 80° C., preferably between 25° ° C. and 70° C., and preferably between 30° ° C. and 60° C.

Advantageously, the solvent fraction resulting from step b) is cooled in step c) to a temperature of at least 40° C., preferably at least 50° C., preferably at least 60° C., preferably at least 70° C. lower relative to the temperature $T_{loop}$ of the cooled liquid fraction in the recirculation loop(s) of the reaction section.

Step d) of Introducing the Fraction Resulting from c)

The process according to the invention therefore comprises a step d) of introducing, into the reaction section of the oligomerization step a), the solvent fraction cooled in step c) to a temperature below the temperature T(loop) of the recirculation loop.

The introduction of the cooled solvent fraction according to the invention makes it possible to partly control the exothermicity of the oligomerization reaction and thus to limit the size of the heat exchanger(s) used in at least one recirculation loop.

Advantageously, the introduction of the cooled solvent fraction is carried out in the reaction section, preferably in the reactor and/or in one or more of the recirculation loops. Preferably, the introduction is carried out in a recirculation loop, advantageously upstream or downstream of the thermal exchanger of said recirculation loop, i.e. upstream or downstream of step a4). Preferably, the introduction of the cooled solvent fraction is carried out in a recirculation loop of the reaction section downstream of the thermal exchanger of said recirculation loop.

Advantageously, the introduction of the cooled solvent fraction downstream of the thermal exchanger of the recirculation loop makes it possible to minimize the temperature difference between the cooled solvent fraction and the liquid fraction of the recirculation loop. This also makes it possible to maximize the use of the exchanger of the recirculation loop(s) and therefore to minimize its size.

Advantageously, the mixture of the solvent fraction cooled in step c) with the liquid fraction circulating, preferably downstream of the thermal exchanger, in the recirculation loop of the reaction section makes it possible to decrease the temperature of the liquid fraction of the recirculation loop by 0.1° C. to 20.0° C., preferably between 0.2° C. and 15.0° C. and preferably between 0.5° ° C. and 10.0° C.

Advantageously, the cooled solvent fraction has a flow rate, as a weight percentage relative to the flow rate of the liquid circulating in the circulation loop, of between 0.05% and 15.0%, preferably between 0.1% and 10.0%, preferably between 0.5% and 8.0%, preferably between 0.8% and 6.0% and preferably between 1.0% and 5.0%.

Thus, the implementation of steps c) and d) according to the invention makes it possible, by means of the cooled solvent fraction, to reduce the energy exchanged in the recirculation loops, and therefore makes it possible to reduce the size of the exchanger. The expected saving may advantageously be of the order of 1% to 50%, preferably between 2% and 30% and preferentially between 3% and 20% over the exchange surface area.

DESCRIPTION OF THE FIGURES

FIGS. 1, 2, 3 and 4 provide schematic illustrations of the particular embodiments of the subject of the present invention, without limiting the scope of said invention.

EXAMPLES

Figure 1:
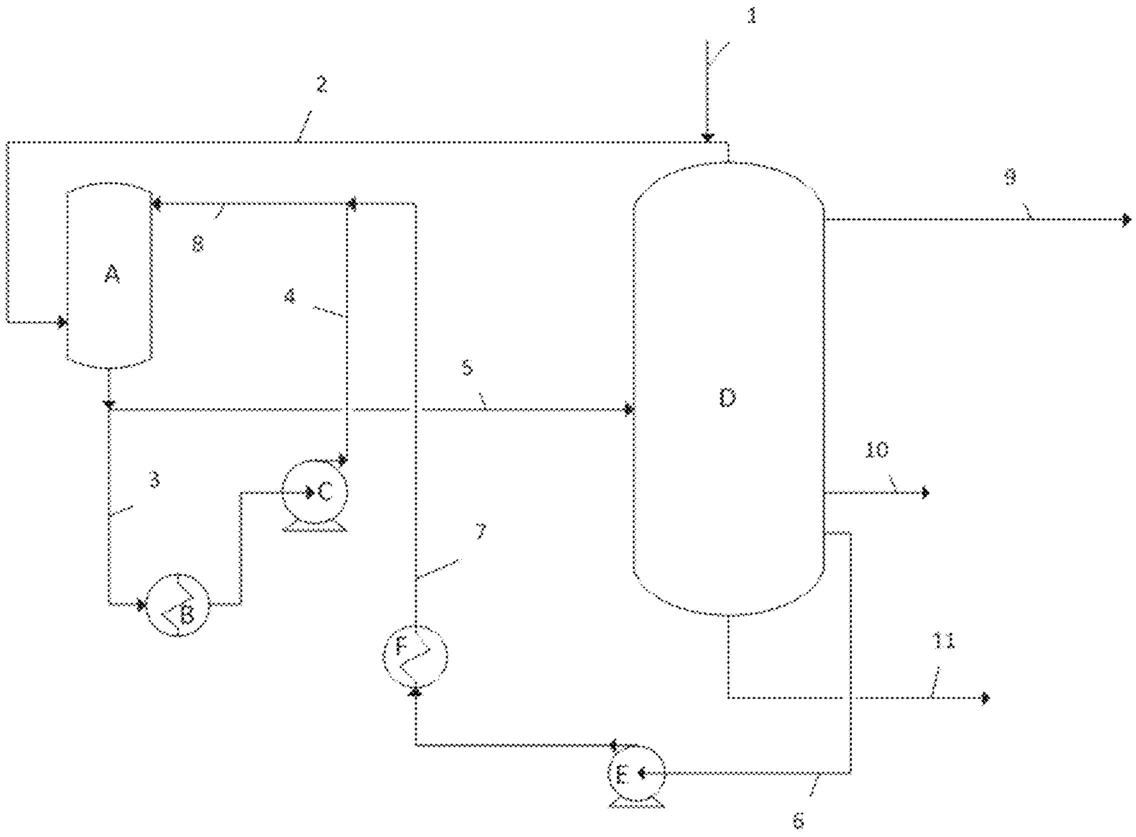
FIG. 1 represents a schematic illustration of a plant carrying out an embodiment of the oligomerization process according to the invention. Said plant comprises a two-phase gas/liquid oligomerization reactor A, the zones of variable diameter of which are not represented, a recirculation loop comprising an exchanger B and a pump C, a separation section D, a pump E for circulating the solvent fraction, an exchanger for cooling the solvent fraction (F). In this plant, the stream 2 is a mixture of the stream 1 of fresh ethylene and of ethylene resulting from the separation section. The stream 2 is introduced into the reactor A. The stream 3 is the liquid-phase fraction withdrawn from the reactor and sent to the recirculation loop comprising an exchanger B and a pump C in order to obtain a cooled liquid fraction 4. The stream 6 is the solvent fraction separated in the separation section D which passes through a pump E and is cooled in an exchanger F to give a cooled solvent fraction 7. The fractions 7 and 4 are mixed to give a stream 8 before being introduced into the reactor A. The stream 5 corresponding to a part of the effluent withdrawn from the reactor A is sent to the separation section D. The separation section makes it possible to obtain the stream 6, a stream 9 corresponding to the light reaction products, a stream 10 corresponding to the heavy reaction products and a stream 11 corresponding to a heavy fraction comprising the spent catalyst.
Figure 2:
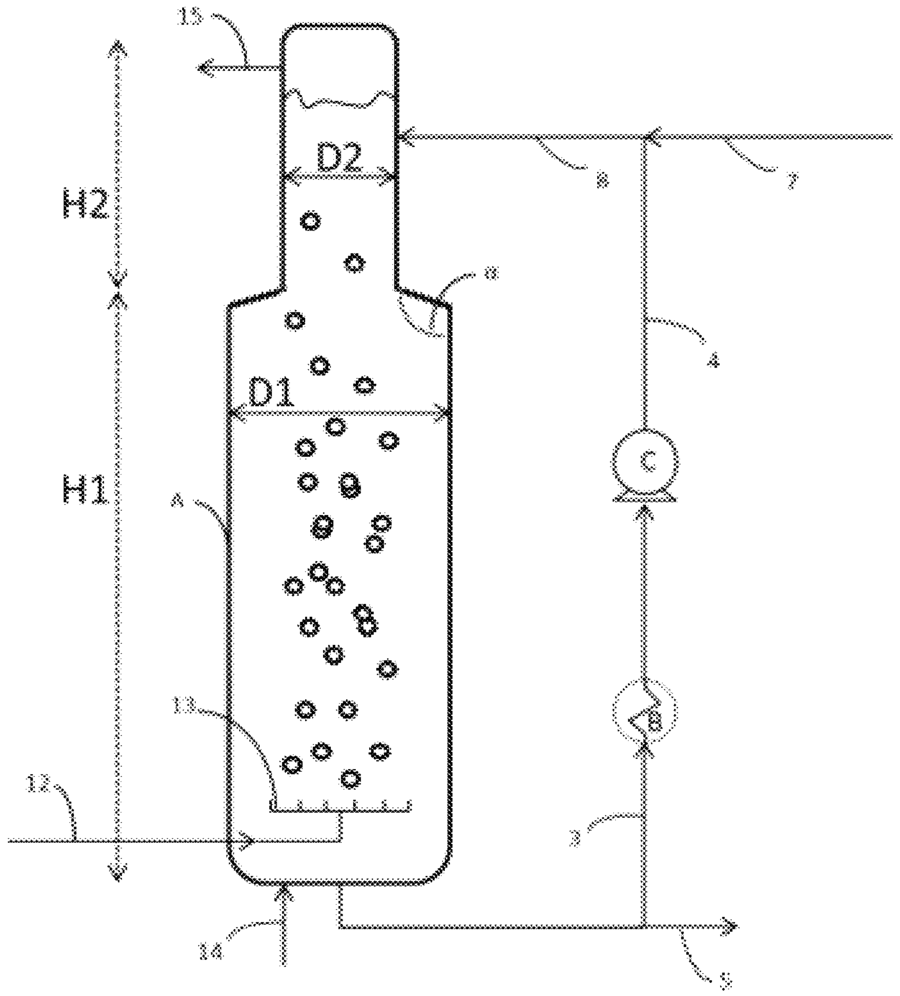
FIG. 2 illustrates a gas/liquid reactor A with consecutive zones of decreasing diameter according to the invention comprising a lower part comprising a liquid phase, an upper part comprising a gas phase, and a means for introducing a gaseous olefinic feedstock 12 by means of a gaseous distributor 13 into the liquid phase. The upper part comprises a bleeding means 15. A fraction divided into two streams is withdrawn from the bottom of reactor A, a first main stream 3 sent to a heat exchanger B and a pump C in order to obtain a cooled fraction 4. The second stream 5 corresponds to the effluent sent to the separation section. The fractions 7 and 4 are mixed in a stream 8 before being introduced into the reactor A. The catalytic system 14 is introduced into the bottom of the reactor. The zone 1 located at the bottom of the reactor has a larger diameter than the zone located at the top of the reactor. The first bottom zone is characterized by its diameter denoted D1 and its height H1, these two parameters defining the volume, denoted V1, of said zone. Similarly, the second zone located at the top is characterized by its height denoted H2 and its diameter denoted D2, which is less than D1, defining the volume, V2, of the second zone. In this embodiment, the two zones making up the reactor A are formed by cylinders of decreasing diameter.
Figure 3:
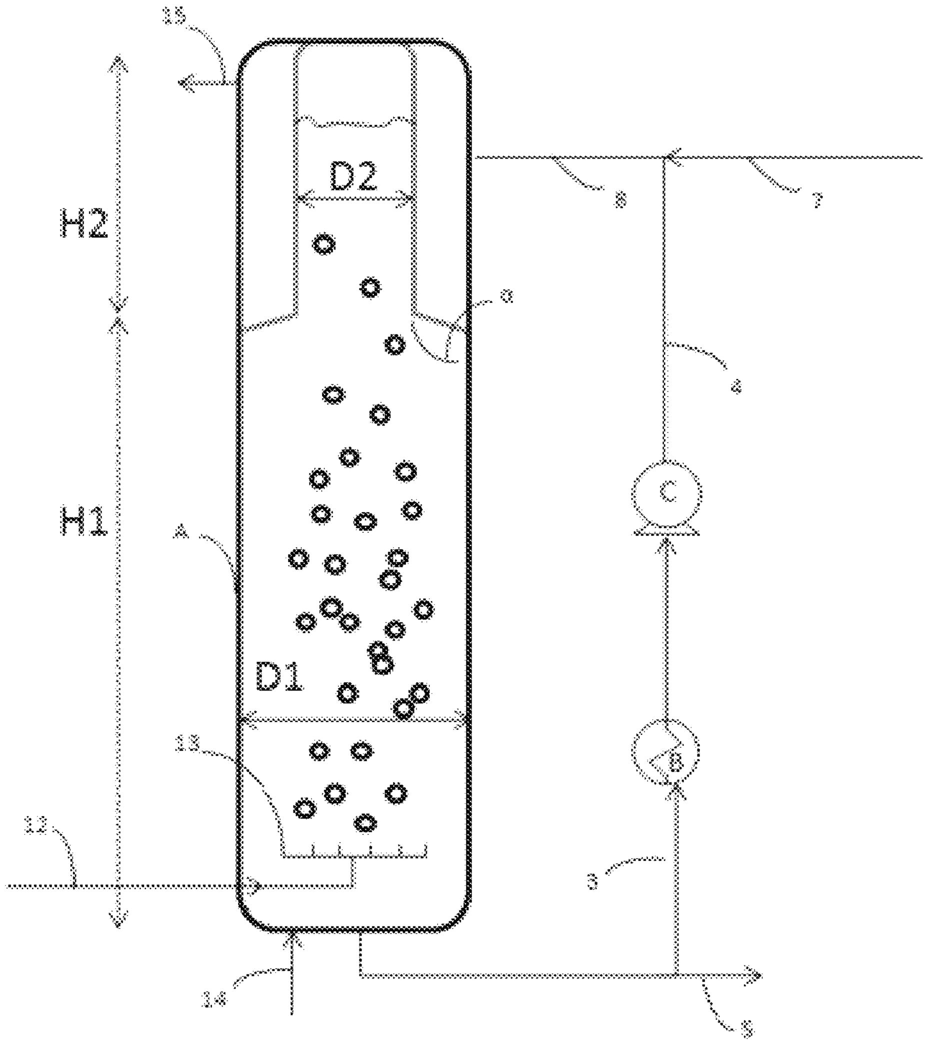
FIG. 3 illustrates another embodiment, which differs from that of FIG. 2 in that the second zone located at the top of the reactor A is delimited by an internal 11 placed inside the reactor A.
Figure 4:
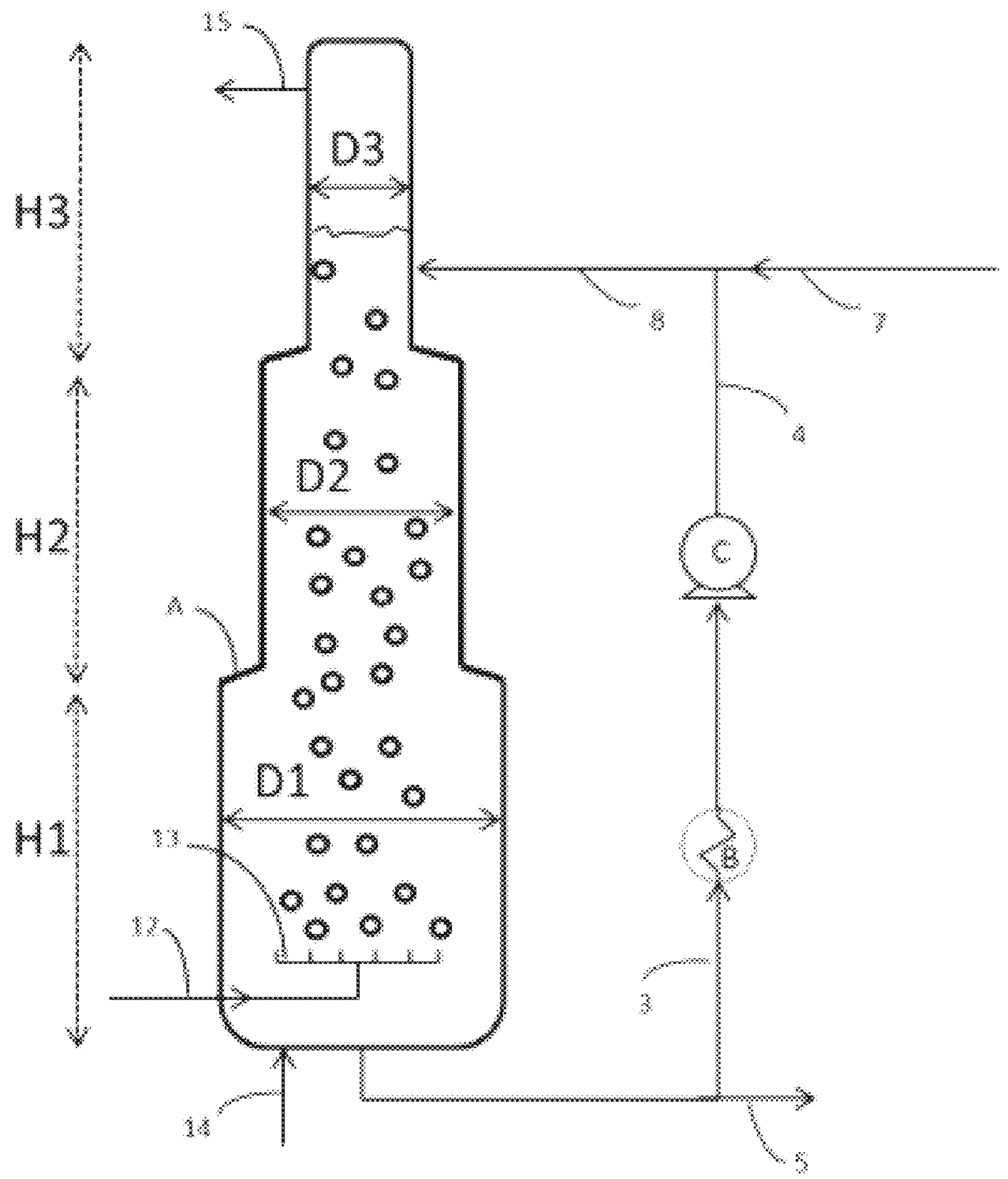
FIG. 4 illustrates another embodiment, which differs from that of FIG. 2 in that the reactor A comprises three consecutive zones of decreasing diameter.

The examples below illustrate the invention without limiting the scope thereof.

The examples below describe a process for the oligomerization of ethylene carried out continuously in a two-phase gas/liquid reactor of bubble column type at a pressure of 6.1 MPa and a temperature of 135° C. The catalytic system is introduced into the reactor at a concentration of 1 ppm by weight of chromium, comprises the chromium precursor Cr(2-ethylhexanoate)$_3$, 2,5-dimethylpyrrole at a molar ratio relative to the chromium of 3, 11 molar equivalents of triethylaluminium and 8 molar equivalents of diethylaluminium chloride relative to the chromium, in the presence of o-xylene as additive at a molar ratio of 500 relative to the chromium, and cyclohexane as solvent.

The amount of cyclohexane, used as solvent 6, introduced into the reactor A is dependent on the amount of ethylene entering the same reactor A (stream 2); the amount of solvent is adjusted so as to have a solvent content of 58% in the reactor.

Example 1 (Comparative)

Example 1 illustrates an oligomerization process according to the prior art in which the solvent fraction (7) is separated in a downstream separation section and recycled to the reaction section without being cooled by a heat exchanger F and in which the oligomerization process uses a gas-liquid reactor of bubble column type.

The catalytic system is brought into contact with gaseous ethylene by introduction of said gaseous ethylene into the lower part of said reactor. The reaction effluent is subsequently recovered at the bottom of the reactor.

The production of hex-1-ene requires the conversion of 14 000 kg/h of ethylene. The flow rate of solvent under the operating conditions adopted is 19 500 kg/h. The temperature of the recycled solvent fraction is 101° C.

The residence time in the reaction section (reactors+recirculation loop(s)) is 40 minutes.

Since the oligomerization reaction is exothermic, the heat of the reaction is removed by heat exchangers placed on recirculation loops outside the reactor, having a total surface area of 1650 $m^2$. The total reaction liquid volume of 41.4 $m^3$ is distributed between the volume taken by the heat exchangers and their recirculation loop, and the reactor. The total reaction liquid volume is broken down in the following manner: 30.4 $m^3$ for the heat exchange loops, and 11.0 $m^3$ for the reactor. The height of liquid in the reactor is then 4.8 metres (denoted m) for a diameter of 1.7 m. The temperature of the mixture 8 of the solvent fraction 7 and of the recirculation fluid 4 is then 120° C. at the reactor inlet. The temperature of the stream 4, corresponding to the stream at the outlet of the exchanger B of the recirculation loop of the reaction section, is then 120.4° C.

The production of hex-1-ene is 9.32 tonnes/hour, the hex-1-ene selectivity is 93.2 wt %.

Example 2 (According to the Invention)

The oligomerization process according to the invention is illustrated in FIG. 1 and is performed under the same conditions as in Example 1. Example 2 comprises a step of cooling the solvent fraction resulting from the separation section before introduction into the reaction section, using an exchanger F, as illustrated in FIG. 1 and a reactor A with zones of variable diameters. Said solvent fraction is cooled to a temperature of 40° C.

The total surface area of the exchangers of the recirculation loops is 1440 $m^2$. Thus, the process according to the invention makes it possible to reduce the exchange surface area of the heat exchangers by approximately 13% (=100×(1650−1440)/1650) compared to the exchange surface area of Example 1, which represents a saving in the operating cost of the unit.

In this example, the residence time is kept identical to that of Example 1, namely 40 minutes (min). The total reaction liquid volume is identical to that of Example 1. The step of cooling the solvent fraction therefore makes it possible to reduce the need for exchange in the recirculation loops, which results in a decrease of the surface area of the exchangers.

Owing to the decrease of the surface area required in the exchangers, the volume of the recirculation loops is reduced by 3% (volume of 29.5 $m^3$). The liquid volume of the reactor may then be increased by 8% (working volume of 11.9 $m^3$) which leads to a gain in the height of liquid of 8%.

Furthermore, the use of a reactor with zones of variable diameters makes it possible to obtain an additional gain of 35% in the height of liquid (total liquid height of 7.1 m). The height of liquid in the lower zone of the reactor is 2.1 m for a diameter of 1.7 m. The height of the upper part of the liquid reactor is then 4.9 m for a diameter of 1.35 m.

The temperature target of the mixture 8 of the solvent fraction 7 and of the liquid fraction 4 circulating in the recirculation loops was kept identical to Example 1, namely 120° C. The temperature of the cooled liquid fraction 4, corresponding to the outlet of the exchanger B, is then 121.9° C.

In addition, the 3% reduction in the volume of the recirculation loops and the use of a gas/liquid reactor with zones of variable diameters also makes it possible to increase the volume of liquid in the reactor by 9% and the liquid height by 47%, thereby making it possible to maximize the ethylene saturation in the liquid contained in the reactor.

The production of hex-1-ene is 9.32 tonnes/hour, the hex-1-ene selectivity is 93.2 wt %.

Example 3 (According to the Invention)

The oligomerization process according to the invention is performed under the same conditions as in Example 2.

The step of cooling the solvent fraction makes it possible to reduce the need for exchange in the recirculation loops, which results in a decrease of the surface area of the exchangers. The solvent fraction is cooled to a temperature of 40° C. The total surface area of the exchangers of the exchange loop is then limited to 1440 $m^2$. Thus, the process according to the invention makes it possible to reduce the exchange surface area of the heat exchangers by approximately 13% (=100×(1650−1440)/1650) compared to the exchange surface area of Example 1, which represents a saving in the operating cost of the unit.

The liquid height in the reactor is kept identical to Example 1. The reactor then comprises two zones, a lower zone 1.6 m high for a diameter of 1.7 m and an upper zone 3.1 m high for a diameter of 1.35 m. Owing to the decrease of the surface area required in the exchangers, the volume of the recirculation loops is reduced by 3% (volume of 29.5 $m^3$). The liquid volume of the reactor with zones of variable diameters is 8.4 $m^3$. The total reaction liquid volume of the reaction section is therefore then 37.8 $m^3$, namely an 8% saving compared to Example 1.

The temperature target of the mixture 8 of the solvent 7 and of the recirculation fluid 4 was kept identical to Example 1, namely 120° C. The temperature of the stream 4, corresponding to the outlet of the exchanger B, is then 121.9° C.

In this example, the residence time is 36.6 minutes. The process according to the invention allows a reduction in the residence time, which leads to a gain in selectivity of 0.1%. This gain enables, for a constant hex-1-ene production, a decrease in the ethylene consumption of 0.1% and therefore a saving in the operating cost of the unit. The decrease in the residence time also enables a saving in the chromium concentration needed for achieving this performance of 8% (corresponding to 4 ppm of chromium), namely a saving in the catalyst consumption and therefore a saving in the operating cost of the unit.

The production of hex-1-ene is 9.32 tonnes/hour, the hex-1-ene selectivity is 93.3 wt %.

The table below summarizes the results obtained for Examples 1 to 3.

| | | Example 1 | Example 2 | Example 3 |
|---|---|---|---|---|
| Temperature of the recycled solvent fraction | ° C. | 101 | 40 | 40 |
| Temperature of the cooled | ° C. | 120.4 | 121.9 | 121.9 |

-continued

| | | Example 1 | Example 2 | Example 3 |
|---|---|---|---|---|
| liquid fraction | | | | |
| Temperature of solvent fraction + cooled liquid fraction | ° C. | 120 | 120 | 120 |
| Exchange surface area of the recirculation loops | $m^2$ | 1650 | 1440 | 1440 |
| Volume of the recirculation loops | $m^3$ | 30.4 | 29.5 | 29.5 |
| Reactor liquid volume | $m^3$ | 11.0 | 11.9 | 8.4 |
| Reaction section volume | $m^3$ | 41.3 | 41.3 | 37.8 |
| Diameter of the lower zone of the Reactor | m | 1.7 | 1.7 | 1.7 |
| Liquid height in the lower zone of the Reactor | m | 4.8 | 2.1 | 1.6 |
| Diameter of the upper zone of the Reactor | m | — | 1.35 | 1.35 |
| Liquid height in the upper zone of the Reactor | | — | 4.9 | 3.1 |
| Total liquid height | | 4.8 | 7.1 | 4.8 |
| Residence time | min | 40 | 40 | 36.6 |
| Selectivity | % | 93.2 | 93.2 | 93.3 |

The invention claimed is:

1. A process for the oligomerization of an olefinic feedstock, comprising:

a) a step of oligomerization of the olefinic feedstock, carried out at a temperature of between 30° C. and 200° C. and a pressure of between 0.1 and 10 MPa, in the presence of a homogeneous catalytic oligomerization system and of a solvent, in a reaction section comprising:

an oligomerization reactor with zones of variable diameter and comprising a liquid phase, and at least one recirculation loop allowing the cooling of at least a part of a liquid-phase fraction to a temperature $T_{loop}$, the oligomerization step a) comprises the following substeps:

step a1) of introducing the homogeneous catalytic oligomerization system, step a2) of bringing into contact with the olefinic feedstock, substep a3) of withdrawing a liquid-phase fraction from the oligomerization reactor, and dividing the liquid-phase fraction into a first liquid stream and a second liquid stream, substep a4) of cooling the first liquid stream in at least one recirculation loop, to a temperature $T_{loop}$, by circulating said first liquid stream through one or more thermal exchangers located in the at least one recirculation loop, step a5) of introducing the cooled first liquid stream into the reactor, b) a step of separating the second liquid stream, in a separation section so as to obtain a solvent fraction, c) a step of cooling the solvent fraction resulting from step b) to a temperature below the temperature $T_{loop}$ to which the first liquid stream is cooled in the least one recirculation loop, d) a step of introducing, into the reaction section of the oligomerization step a), the cooled solvent fraction resulting from step c), wherein the reactor with zones of variable diameter comprises n consecutive zones, n being a positive integer between 2 and 10, with:

for each of the n zones having a diameter Dn which decreases in the direction of the bottom zone to the top zone of said reactor, a ratio (Dn/Dn−1) of the diameter of the upper zone, denoted Dn, to the diameter of the adjacent lower zone, denoted Dn-1, of less than or equal to 0.9, for a given zone, a ratio of the volume of said zone, denoted Vn, to the total volume of the reaction chamber, denoted Vtot, of between 0.2 and 0.8, the n consecutive zones are arranged in series along the vertical axis of the reactor so as to define zones in the reaction enclosure having diameters decreasing from the bottom to the top of the reactor and thus to increase the height of the liquid phase which may be contained in the reactor compared to the height of a constant-diameter reactor, and thus to increase the time during which the olefinic feedstock is present in the liquid phase.

2. The process according to claim 1, in which the reactor with zones of variable diameter comprises n consecutive zones, n being a positive integer between 2 and 5, with:

the ratio (Dn/Dn−1) of between 0.3 and 0.7, for a given zone, the ratio of the volume of said zone, denoted Vn, to the total volume of the reaction chamber, denoted Vtot, of between 0.35 and 0.65.

3. The process according to claim 1, in which the solvent fraction resulting from step b) is cooled in step c) to a temperature of between 0° C. and 150° C.

4. The process according to claim 1, in which the solvent fraction resulting from step b) is cooled in step c) to a temperature at least 40° C. lower relative to the temperature $T_{loop}$ of the liquid-phase fraction cooled in the at least one recirculation loop.

5. The process according to claim 4, in which step d) of introducing at least a part of the cooled solvent fraction is carried out in a recirculation loop upstream or downstream of a thermal exchanger of the at least one recirculation loop.

6. The process according to claim 4, in which step d) of introducing at least a part of the cooled solvent fraction is carried out in a recirculation loop downstream of a thermal exchanger of the at least one recirculation loop.

7. The process according to claim 1, in which the cooling of the solvent fraction in step c) is carried out by one or more thermal exchangers.

8. The process according to claim 1, in which the separation section comprises at least two distillation columns.

9. The process according to claim 1, in which step d) of introducing the cooled solvent fraction is carried out in the reactor and/or in one or more of the recirculation loops.

10. The process according to claim 1, in which the cooled solvent fraction has a flow rate, as a weight percentage relative to the flow rate of the liquid-phase fraction circulating in the at least one recirculation loop, of between 0.05% and 15.0%.

11. The process according to claim 1, in which the olefinic feedstock comprises olefins having between 2 and 6 carbon atoms.

12. The process according to claim 1, in which the thermal exchanger(s) used in substep a4) decreases the temperature of the liquid-phase fraction withdrawn in substep a3) by 1.0 to 30.0° C.

13. The process according to claim 1, in which the cooling of the solvent fraction in step c) is carried out by one or more heat exchangers of process fluid/process fluid type, of air cooler type, and/or of cooling water exchanger type.

14. The process according to claim 1, in which the separation section comprises at least three distillation columns.

15. The process according to claim 1, in which the separation section comprises at least four distillation columns.

16. The process according to claim 1, in which the cooled solvent fraction has a flow rate, as a weight percentage relative to the flow rate of the liquid-phase fraction circulating in the at least one recirculation loop, of 0.1% and 10.0%.

17. The process according to claim 1, in which the olefinic feedstock comprises olefins having between 2 and 4 carbon atoms.

* * * * *